| United States Patent [19] | [11] | 4,413,140 |
|---|---|---|
| Fozzard | [45] | Nov. 1, 1983 |

[54] LIQUID EXTRACTION OF DIACETOXYBUTANE WITH HALOGENATED PARAFFINS

[75] Inventor: George B. Fozzard, Bartlesville, Okla.

[73] Assignee: Phillips Petroleum Company, Bartlesville, Okla.

[21] Appl. No.: 791,106

[22] Filed: Apr. 26, 1977

[51] Int. Cl.³ .................. C07C 67/58; C07C 69/16; C07C 27/02; C07C 27/34; C07C 51/48; C07C 53/08

[52] U.S. Cl. .................. 560/248; 560/263; 562/607; 562/608; 568/858; 568/868

[58] Field of Search ............... 560/248, 263; 260/541, 260/637, 635; 562/607, 608; 568/858, 868

[56] References Cited

U.S. PATENT DOCUMENTS

| 2,366,667 | 1/1945 | Deebel | 560/236 |
|---|---|---|---|
| 3,859,368 | 1/1975 | Kollar | 560/263 |
| 3,917,720 | 11/1975 | Webb et al. | 560/236 |
| 4,010,197 | 3/1977 | Toriya et al. | 560/263 |
| 4,012,424 | 3/1977 | Sherwin et al. | 560/263 |

Primary Examiner—Vivian Garner

[57] ABSTRACT

A solvent comprising at least one aromatic hydrocarbon and/or halogenated paraffin is used in a liquid extraction process for extracting diesters from mixtures comprising diesters, the corresponding monoesters and acids, diols and water.

6 Claims, 1 Drawing Figure

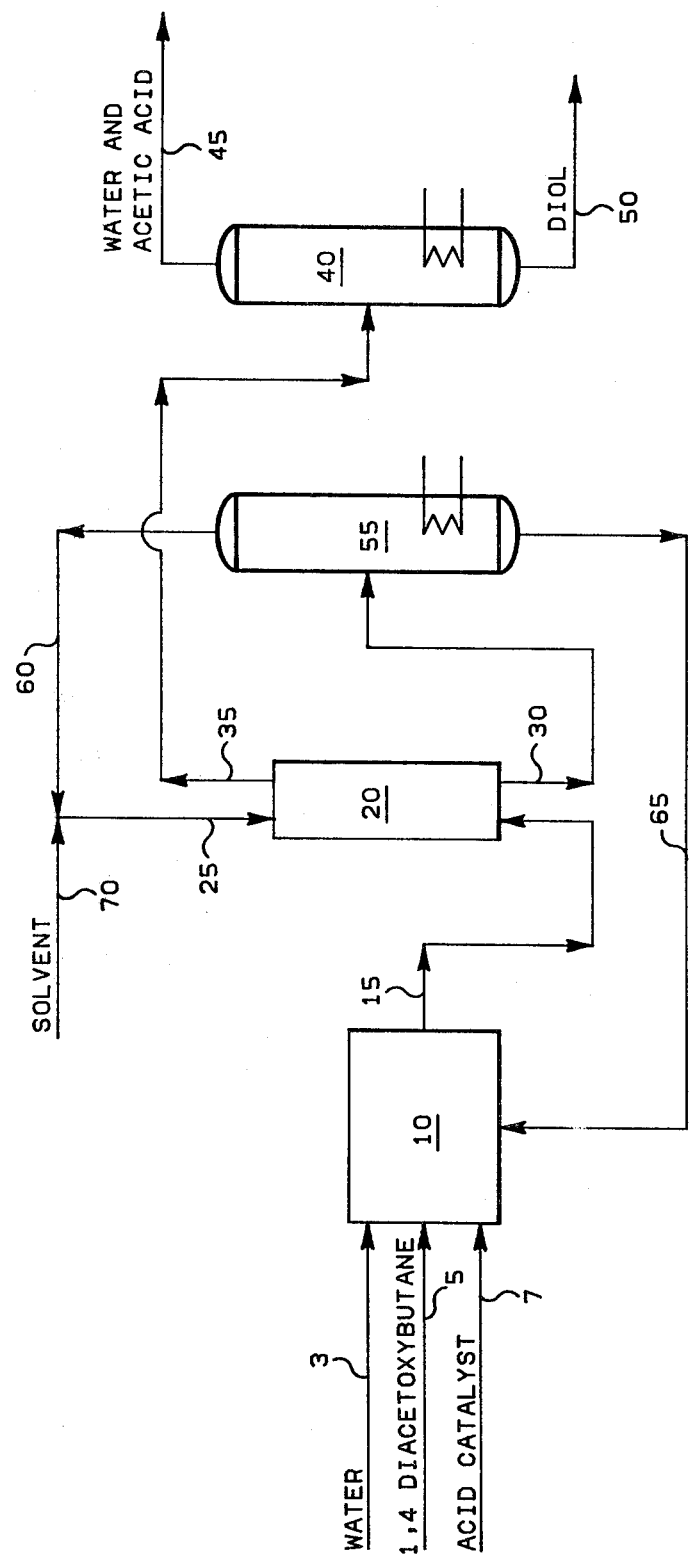

LIQUID EXTRACTION OF DIACETOXYBUTANE WITH HALOGENATED PARAFFINS

BACKGROUND OF THE INVENTION

This invention pertains to a separation process. In particular, it pertains to a liquid extraction process for the separation of diesters.

In chemical operations it is often desirable to separate diesters from a solution that includes diesters, the corresponding monoesters and acids, diols and water. For example, in a process for the continuous production of a diol from a diol ester as disclosed in U.S. Pat. No. 3,917,720, the effluent stream from the reactor contains water, acetic acid, diol, monoesters, and diesters. The diesters are removed from the effluent stream by first flashing off the water and acetic acid and then extracting esters from the remaining mixture using a chloroform/water mixture as solvent.

The present invention provides an improved method for the solvent extraction of diesters from mixtures comprising diesters, the corresponding monoesters and acids, diols and water with solvents that selectively extract diesters from mixtures containing same.

Thus, one object of the present invention is to provide an energy efficient method for separating diesters from complex mixtures containing same.

Another object of the invention is to provide a process for separating diesters from liquid mixtures, which utilizes relatively inexpensive equipment.

A further object of the invention is to provide a process for the solvent recovery of diesters from mixtures containing same.

Still another object of the invention is to provide an improved process for the separation of diesters from diol reaction products.

A still further object of the invention is to efficiently remove diester impurities from diol reaction products containing same.

A still further object of the invention is to provide a one-step process for the solvent extraction of diesters.

Other objects of the invention will become apparent to those skilled in the art by studying this disclosure.

SUMMARY OF THE INVENTION

In accordance with one aspect of this invention, at least one aromatic hydrocarbon is used as a selective solvent in a liquid extraction process to extract diesters from a mixture comprising diesters, the corresponding monoesters and organic acids, diols and water.

In accordance with another aspect of the invention, at least one halogenated paraffin is used as a selective solvent in a liquid extraction process to extract diesters from a mixture comprising diesters, the corresponding monoesters and organic acids, diols and water.

In accordance with a further aspect of the invention, a mixture of at least one halogenated paraffin and at least one aromatic hydrocarbon is used as a selective solvent in a liquid extraction process to extract diesters from a solution comprising diesters, the corresponding monoesters and organic acids, diols and water.

In accordance with still another aspect of the invention, diacetate is hydrolyzed in a reaction zone in the presence of an acid catalyst to form butanediol. The unreacted diacetate is separated from the reaction products which include diacetates, monoacetates, water, diol, and acetic acid by liquid extraction using a solvent comprising at least one compound selected from halogenated paraffins and aromatic hydrocarbons. The solvent is then removed from the solvent-diacetate mixture and the diacetate is recycled to the reaction zone.

In accordance with a still further aspect of the invention, 1,4-diacetoxybutane is mixed with water and an acid catalyst in a reaction zone under conditions favoring conversion of diacetate to diol. The products of the reaction which include 1,4-diacetoxybutane, 1,4-butanediol, 4-acetoxy-1-butanol, acetic acid, and water are then contacted with a solvent selected from halogenated paraffins and aromatic hydrocarbons. The solvent is used to selectively remove, in a liquid extraction process, 1,4-diacetoxybutane from the reaction products. The solvent is then separated from 1,4-diacetoxybutane by a convenient method such as fractional distillation and the diacetate is recycled to the reaction zone.

Other aspects of the invention will become apparent to those skilled in the art upon studying this disclosure.

DETAILED DESCRIPTION OF THE INVENTION

It has been discovered that aromatic hydrocarbons and halogenated paraffins, and mixtures of these, can be utilized as selective solvents in liquid extraction processes for separating diesters from solutions comprising diesters, the corresponding monoesters and acids, diols and water. The invention is applicable to the separation of diesters of organic acids having from 1 to 3 carbon atoms and diols having from 3 to 5 carbon atoms, and the separation involves these diesters, the corresponding monoesters and acids, diols as defined, and water. The method of this invention can be utilized in any chemical process in which the separation described above is required; however, the method is particularly useful and will be described in detail in connection with the process for production of diols from diol esters.

Referring now to the FIGURE, water, diol ester, such as 1,4-diacetoxybutane, and a mineral acid catalyst, if a solid heterogeneous catalyst is not used, are charged into reactor 10 by lines 3, 5, and 7, respectively, and the reactants are mixed under such reaction conditions as to convert at least a portion of the diol ester to diol. The reaction effluent, usually containing water, acetic acid, diol, monoacetates, and diacetates, is removed from reactor 10 and introduced via line 15 into a countercurrent liquid extraction zone 20. If the diol ester charged into reactor 10 is 1,4-diacetoxybutane, then the effluent comprises 1,4-diacetoxybutane, water, acetic acid, 1,4-butanediol and the monoester 4-acetoxy-1-butanol.

In extraction zone 20 the reaction effluent from zone 10 is contacted with a solvent, comprising at least one aromatic hydrocarbon and/or halogenated paraffin, introduced via 25. Extraction zone 20 is operated under conditions such that the solvent or solvent mixture selectively dissolves the diesters and the solvent containing dissolved diester is withdrawn via line 30. The remainder of the reaction effluent is removed overhead and transported via line 35 to a first fractionator 40 and therein subjected to such distillation conditions including temperature and pressure as to separate the reaction effluent feed into an overhead stream 45 containing mainly water and acetic acid and a bottoms stream 50 containing diol and monoacetate.

The solvent-diester mixture removed as bottoms from extraction zone 20 in line 30 is passed to a second fractionator 55 which is maintained under such distillation conditions as to cause separation of the mixture into solvent which is taken off as an overhead by line 60 and diester which is removed as a bottoms product and recycled to reactor 10 via line 65. The solvent withdrawn by 60 is combined with make-up solvent in line 70 to form the solvent stream 25.

The solvent used in the process is at least one compound selected from aromatic hydrocarbons and halogenated paraffins. Suitable solvents that can be used include aromatic hydrocarbon having up to and including 10 carbon atoms and halogenated paraffins, especially chlorinated paraffins, that have normal boiling points below about 392° F. (200° C.). Especially useful as solvents are benzene, toluene, the xylenes, ethylbenzene, isopropylbenzene, 1-methyl-4-ethylbenzene, 2-chloropropane, 2-bromo-1-chlorobutane, 1,4-dichloropentane, and the like, and mixtures thereof.

The weight ratio of solvent to the reaction effluent with which it is contacted under extraction conditions can vary over a considerable range depending on the specific process and economic considerations. The usual weight ratio is between about 1:10 and about 10:1.

The reactor 10 is any conventional reactor that can be used for the hydrolysis reaction. For the system depicted in the FIGURE, it is preferred to use a stirred tank reactor. Typical hydrolysis conditions include a temperature between about 122° F.–302° F. (50° C.–150° C.) and a pressure between about 5 psia and 500 psia (0.034 MPa–3.4 MPa). The details of a typical hydrolysis operation are included in the disclosure of U.S. Pat. No. 3,917,720 which is incorporated herein by reference.

The extractor is also a conventional piece of equipment. The choice of a particular type of extractor depends largely on economic considerations and the desired degree of separation. A single stage mixer-settler type device can be employed if a high purity product is not essential, whereas multi-stage equipment is used in applications that require high purity product. In most applications, due to good mass transfer efficiency, a countercurrent multi-stage column is preferred. The usual operating conditions employed in a countercurrent extraction process depicted in the FIGURE are sufficient to selectively dissolve the diesters from mixtures containing same and typically about 15 psia (0.10 MPa) and 77° F. (25° C.).

The conditions in fractionators 40 and 55 can vary considerably depending on the separation desired; however, the usual conditions in zone 40 include a pressure of 10–50 psia (0.069–0.34 MPa) and a temperature range of 212°–302° F. (100°–150° C.); and in zone 55 a pressure ranging from 10–50 psia (0.069–0.34 MPa) and a temperature in the range of 257°–392° F. (125°–200° C.).

Many changes and modifications will occur to those skilled in the art upon studying this specification and the appended claims. For example, in some applications it may be preferable to separate water and organic acid prior to the treatment of the effluent in the liquid extraction zone.

EXAMPLE

A solution having known concentration of water, acetic acid, 1,4-diacetoxybutane, monoacetate, and 1,4-butanediol was placed in a flask. A solvent was added to the solution and the entire content of the flask was mixed thoroughly by vigorous shaking. The liquid was then allowed to settle and separate into two distinct phases—the extract and the raffinate. Each phase was then analyzed to determine the concentration of each of the components present therein. The results are summarized in the Table.

TABLE

| Composition Wt. % | Water | Acetic Acid | Butanediol | Mono-Acetate | Diacetate | Solvent |
|---|---|---|---|---|---|---|
| n-Hexane Extraction | | | | | | |
| Feed | 56.8 | 12.3 | 13.3 | 1.5 | 15.6 | — |
| Extract | .1 | .1 | — | — | 4.8 | 94.9 |
| Raffinate | 61.9 | 10.1 | 14.3 | .9 | 10.0 | 61.9 |
| Cyclohexane Extraction | | | | | | |
| Feed | 54.6 | 11.7 | 14.3 | 1.6 | 16.2 | — |
| Extract | — | — | — | — | 4.7 | 95.1 |
| Raffinate | 61.8 | 12.0 | 15.4 | 1.1 | 8.6 | 1.0 |
| Benzene Extraction | | | | | | |
| Feed | 38.7 | 19.3 | 18.8 | 1.1 | 22.0 | — |
| Extract | .6 | 2.4 | 0.2 | — | 7.9 | 88.9 |
| Raffinate | 51.4 | 17.2 | 24.6 | 1.5 | 1.6 | 3.7 |
| Toluene Extraction | | | | | | |
| Feed | 37.7 | 16.3 | 19.1 | 2.4 | 24.3 | — |
| Extract | .4 | 2.0 | .1 | — | 8.4 | 89.0 |
| Raffinate | 47.9 | 16.3 | 25.3 | 3.4 | 2.4 | 4.6 |
| 2-Chloropropane | | | | | | |
| Feed | 58.4 | 12.4 | 13.4 | 0.9 | 14.9 | — |
| Extract | 2.2 | — | — | — | 7.1 | 82.5 |
| Raffinate | 66.1 | 9.2 | 15.8 | 1.1 | 1.4 | 6.2 |

The data demonstrate the feasibility of using benzene, toluene, and 2-chloropropane for liquid extraction of diacetate from a mixture comprising water, acetic acid, butanediol, monoacetate, and diacetate. After a single extraction with benzene, the concentration of diacetate in the extract was 7.9 and in the raffinate it was 1.6. The corresponding concentrations after toluene and 2-chloropropane extractions were 8.4 and 7.1 in the extract and 2.4 and 1.4 in the raffinate, respectively.

Similar extractions with n-hexane and cyclohexene were much less successful yielding diacetate concentrations of 4.8 and 4.7 in the extract and 10.0 and 8.6 in the raffinate, respectively.

I claim:
1. A process for separating 1,4-diacetoxybutane from a mixture comprising 1,4-diacetoxybutane, 4-acetoxy-1-butanol, 1,4-butanediol, acetic acid, and water, which comprises the steps of:
   (a) contacting said mixture in a liquid extraction zone with at least one solvent selected from halogenated paraffins having normal boiling points below about 392° F. under conditions which produce an extract containing 1,4-diacetoxybutane and solvent and a raffinate containing water, 1,4-butanediol, acetic acid, and 4-acetoxy-1-butanol;
   (b) withdrawing from the liquid extraction zone said extract and said raffinate; and
   (c) separating said withdrawn extract into solvent and 1,4-diacetoxybutane.
2. A process according to claim 1 wherein said separating step (c) comprises:
   passing said withdrawn extract to a fractionation zone and therein subjecting it to such distillation conditions including temperature and pressure as to separate said extract into an overhead comprising solvent and a bottoms stream comprising 1,4-diacetoxybutane.
3. A process according to claim 2 further comprising: hydrolyzing 1,4-diacetoxybutane in the presence of an acid catalyst in a reaction zone prior to contacting step (a) and recycling 1,4-diacetoxybutane separated from said fractionation zone to the reaction zone.

4. A process according to claim 3 further comprising:
passing said raffinate to a distillation zone and therein subjecting same to such distillation conditions including temperature and pressure as to separate it into an overhead containing water and acetic acid and a bottoms stream containing 1,4-butanediol and 4-acetoxy-1-butanol.

5. A process according to claim 4 further comprising:
recycling said overhead to the reaction zone.

6. A process according to claim 1 wherein said solvent is 2-chloropropane.

* * * * *